United States Patent
Liou et al.

(10) Patent No.: US 7,806,079 B2
(45) Date of Patent: Oct. 5, 2010

(54) POULTRY SELECTION METHOD TO IMPROVE THE EGG PRODUCTION RATE

(75) Inventors: Ming-Li Liou, Hsinchu (TW);
Chuan-Yi Tang, Hsinchu (TW);
Yen-Jen Lin, Hsinchu (TW); Jyh-Hung Lin, Miaoli County (TW); Chin-Kai Chuang, Miaoli County (TW);
Wen-Chuan Lee, Hsinchu (TW)

(73) Assignees: National Tsing Hua University, Hsin Chu (TW); Animal Technology Institute Taiwan, Miaoli County (TW)

( * ) Notice: Subject to any disclaimer, the term of this patent is extended or adjusted under 35 U.S.C. 154(b) by 344 days.

(21) Appl. No.: 12/214,527

(22) Filed: Jun. 19, 2008

(65) Prior Publication Data

US 2009/0151640 A1    Jun. 18, 2009

(30) Foreign Application Priority Data

Dec. 12, 2007  (TW) .............................. 96147485 A

(51) Int. Cl.
*A01K 45/00* (2006.01)
(52) U.S. Cl. ..................................................... 119/6.8
(58) Field of Classification Search .................. 119/6.8, 119/174, 345; 700/108, 109, 90
See application file for complete search history.

(56) References Cited

U.S. PATENT DOCUMENTS

| 2,385,117 | A | * | 9/1945 | Turner et al. .................... 514/5 |
| 3,382,846 | A | * | 5/1968 | Roncari et al. ................ 119/6.8 |
| 3,703,051 | A | * | 11/1972 | Weinberger ............... 47/58.1 R |
| 4,604,968 | A | * | 8/1986 | Christensen ................. 119/6.8 |
| 6,167,317 | A | * | 12/2000 | Meron et al. ................... 700/32 |
| 6,509,375 | B1 | * | 1/2003 | Meier et al. .................. 514/538 |
| 6,706,291 | B1 | * | 3/2004 | Ishihara et al. .............. 424/729 |
| 2002/0157613 | A1 | * | 10/2002 | Phelps et al. ................. 119/6.8 |
| 2004/0199275 | A1 | * | 10/2004 | Berckmans et al. ........... 700/90 |
| 2005/0065736 | A1 | * | 3/2005 | Bauck et al. ................... 702/20 |
| 2005/0072367 | A1 | * | 4/2005 | El Halawani et al. ....... 119/174 |
| 2006/0260557 | A1 | * | 11/2006 | McCabe et al. ............. 119/174 |
| 2009/0011447 | A1 | * | 1/2009 | Banoub et al. ................. 435/13 |

* cited by examiner

*Primary Examiner*—Rob Swiatek
*Assistant Examiner*—Ebony Evans
(74) *Attorney, Agent, or Firm*—Kusner & Jaffe

(57) ABSTRACT

The present invention discloses a poultry selection method to improve the egg production rate, the method comprises steps of collecting protein samples and egg productivity information of multiple poultry groups, transforming these information into multiple scores, ranks, and their corresponding codes; the next step is to combine the corresponding codes to form regional codes, and compare the matching rate; and select the poultry with the required egg production. The present invention further discloses another method, comprising: the collecting and ranking of protein samples and egg productivity information of known and unknown poultry groups to sort out the ratings; select a poultry group having the required egg production from the known group; define the regional codes based on the ratings of the known group; compare the ratings between the known and unknown groups, select the poultry (from the unknown group) with the same regional codes to the previously selected poultry group with required egg production; and select the poultry with required egg production according to the matching rate after the comparison.

27 Claims, 12 Drawing Sheets

```
┌─────────────────────────────────────────────────┐
│ Collecting and ranking the protein samples and  │
│  the egg production rate information of known   │
│    and unknown poultry groups to sort out the   │
│                   ratings S30                   │
└─────────────────────────────────────────────────┘
                         │
                         ▼
┌─────────────────────────────────────────────────┐
│  Select a poultry group with low egg production │
│        rate from the known groups S32           │
└─────────────────────────────────────────────────┘
                         │
                         ▼
┌─────────────────────────────────────────────────┐
│ Based on the ratings of known poultry groups to │
│         define the regional codes S34           │
└─────────────────────────────────────────────────┘
                         │
                         ▼
┌─────────────────────────────────────────────────┐
│        Compare the ratings between known and    │
│  unknown groups, and from the unknown groups,   │
│  select the poultry with the same regional codes│
│       as the low egg production poultry S36     │
└─────────────────────────────────────────────────┘
                         │
                         ▼
┌─────────────────────────────────────────────────┐
│       Select the poultry with the required egg  │
│ production rate based on the comparison results │
│        of regional codes' matching rate S38     │
└─────────────────────────────────────────────────┘
```

FIG. 2

| Poultry No. | Total Egg No. | Apo A-I | | Apo VLDL-II | | X-protein | | Vitellogenin | |
|---|---|---|---|---|---|---|---|---|---|
| | | Score | Rank | Score | Rank | Score | Rank | Score | Rank |
| 20 | 37 | 1.21 | 46 | 1.07 | 75 | 1.21 | 19 | 2.68 | 76 |
| 65 | 54 | 3.25 | 75 | 0.05 | 5 | 0.57 | 4 | -0.05 | 5 |
| 3 | 59 | 4.34 | 78 | -0.03 | 1 | 0.43 | 2 | -0.07 | 2 |
| 23 | 61 | 3.42 | 76 | 0.03 | 4 | 1.2 | 18 | 0.01 | 9 |
| 64 | 64 | 2 | 72 | 0.83 | 70 | 2.13 | 71 | 0.83 | 23 |
| 36 | 72 | 0.66 | 8 | 0.21 | 17 | 1.36 | 32 | 2.21 | 67 |
| 45 | 72 | 3.8 | 77 | 0.07 | 7 | 0.83 | 7 | -0.01 | 7 |
| 70 | 75 | 2.33 | 73 | 0.06 | 6 | 2.27 | 77 | 1.45 | 49 |
| 28 | 75 | 3 | 74 | -0.01 | 2 | 0.47 | 3 | -0.05 | 4 |
| 26 | 80 | 0.78 | 19 | 0.87 | 72 | 0.79 | 6 | 2.24 | 70 |
| 22 | 83 | 1.31 | 57 | 0.43 | 42 | 1.31 | 27 | 2.09 | 64 |
| 59 | 88 | 0.66 | 9 | 0.33 | 34 | 1.75 | 56 | 0.95 | 29 |
| 57 | 89 | 0.55 | 3 | 0.32 | 32 | 1.83 | 59 | 0.61 | 15 |
| 17 | 89 | 1.09 | 35 | 1.23 | 78 | 1.5 | 43 | 1.99 | 62 |

FIG. 3

| Poultry No. | Apo A-I | | | | Apo VLDL-II | | | | X-protein | | | | Vitellogenin | | | |
|---|---|---|---|---|---|---|---|---|---|---|---|---|---|---|---|---|
| | Score | Rank | $R_{Bt}$ | $T_{Bii}$ | Score | Rank | $R_{Bt}$ | $T_{Bii}$ | Score | Rank | $R_{Bt}$ | $T_{Bii}$ | Score | Rank | $R_{Bt}$ | $T_{Bii}$ |
| 1 | 2.00 | 63 | 63.82 | 1.62 | 0.92 | 61 | 62.61 | 0.65 | 1.78 | 24 | 39.83 | 1.99 | 5.62 | 63 | 64.66 | 2.58 |
| 2 | 1.05 | 25 | 25.32 | 0.93 | 0.44 | 26 | 26.68 | 0.32 | NA* | — | — | — | 2.71 | 18 | 18.47 | 1.23 |
| 3 | 1.08 | 29 | 29.38 | 0.95 | 0.40 | 21 | 21.55 | 0.29 | 1.24 | 11 | 18.26 | 0.62 | 2.5 | 16 | 16.42 | 1.13 |
| 4 | 1.33 | 50 | 50.65 | 1.13 | 0.49 | 31 | 31.82 | 0.35 | 1.70 | 19 | 31.53 | 1.79 | 4.97 | 53 | 54.39 | 2.28 |
| 5 | 1.18 | 40 | 40.52 | 1.02 | 0.60 | 38 | 39.00 | 0.42 | 1.92 | 34 | 56.43 | 2.35 | 4.83 | 52 | 53.37 | 2.22 |
| 6 | 1.41 | 54 | 54.70 | 1.19 | 0.68 | 45 | 46.18 | 0.48 | NA | — | — | — | 4.24 | 41 | 42.08 | 1.94 |
| 7 | 2.60 | 68 | 68.88 | 2.06 | 0.02 | 4 | 4.11 | 0.03 | NA | — | — | — | 1.12 | 7 | 7.18 | 0.49 |
| 8 | 0.88 | 13 | 13.17 | 0.80 | 1.53 | 73 | 74.92 | 1.06 | 1.84 | 28 | 46.47 | 2.15 | 6.75 | 76 | 78.00 | 3.11 |
| 9 | 2.90 | 71 | 71.92 | 2.28 | 0.22 | 12 | 12.32 | 0.17 | NA | — | — | — | 1.2 | 11 | 11.29 | 0.53 |
| 10 | 1.19 | 44 | 44.57 | 1.03 | 0.64 | 42 | 43.11 | 0.45 | 2.04 | 39 | 64.72 | 2.66 | 4.97 | 54 | 55.42 | 2.28 |
| ⋮ | ⋮ | ⋮ | ⋮ | ⋮ | ⋮ | ⋮ | ⋮ | ⋮ | ⋮ | ⋮ | ⋮ | ⋮ | ⋮ | ⋮ | ⋮ | ⋮ |
| 78 | 4.15 | 75 | 75.97 | 3.19 | 0.02 | 5 | 5.13 | 0.03 | 0.66 | 7 | 11.62 | -0.86 | 0.96 | 5 | 5.13 | 0.42 |

FIG. 4

| Breeding Weeks | | 14 | | | | 24 | | | | 35 | | | |
|---|---|---|---|---|---|---|---|---|---|---|---|---|---|
| | Batch | Mean | S.D. | P | d.o.f | Mean | S.D. | P | d.o.f | Mean | S.D. | P | d.o.f |
| Apo A-I | A | 2.63 | 0.35 | | | 0.20 | 0.19 | | | 1.5 | 0.98 | | |
| | B | 1.73 | 0.74 | 0.000 | 111 | 0.38 | 0.30 | 0.000 | 129 | 1.26 | 0.72 | 0.080 | 139 |
| Apo VLDL-II | A | 0.04 | 0.08 | | | 2.72 | 1.67 | | | 0.64 | 0.43 | | |
| | B | 0.04 | 0.05 | 0.608 | 117 | 2.21 | 1.08 | 0.027 | 130 | 0.45 | 0.3 | 0.003 | 132 |
| X protein | A | 0.60 | 0.21 | | | 0.20 | 0.19 | | | 1.58 | 0.58 | | |
| | B | 0.25 | 0.29 | 0.000 | 136 | 0.38 | 0.30 | 0.000 | 149 | 1.49 | 0.46 | 0.384 | 80 |
| Vitellogenin | A | — | — | | | 0.81 | 0.91 | | | 2.71 | 1.68 | | |
| | B | — | — | — | — | 1.04 | 0.78 | 0.093 | 147 | 1.23 | 0.78 | 0.000 | 105 |

FIG. 6

|  | Batch A | | | Batch B | | |
| --- | --- | --- | --- | --- | --- | --- |
|  | 14w | 24w | 35w | 14w | 24w | 35w |
| Apo A-I | 0.02 | 0.07 | (-0.55)** | 0.16 | 0.2 | (-0.57)** |
| Apo VLDL-II | 0.02 | 0.15 | 0.06 | -0.15 | 0.2 | 0.38** |
| X protein | 0.04 | 0.05 | 0.24* | -0.16 | 0.13 | 0.46** |
| Vitellogenin | — | 0.03 | 0.19 | — | 0.24* | 0.65** |

|  | 14 weeks | 24 weeks | 35 weeks |
|---|---|---|---|
| 20%* | | | |
| 100% code-match[a] | 2/6 | - | 4/5 |
| 50%* | | | |
| 100% code-match | 5/6 | - | 4/5 |

FIG. 8A

|  | 14 weeks | 24 weeks | 35 weeks |
|---|---|---|---|
| 20%* | | | |
| 100% code-match[a] | 2/5 | 0/1 | 4/5 |
| 50%* | | | |
| 100% code-match | 4/5 | 1/1 | 4/5 |

FIG. 8B

POULTRY SELECTION METHOD TO IMPROVE THE EGG PRODUCTION RATE

FIELD OF THE INVENTION

The present invention relates to a poultry selection method, especially relating to a poultry selection method to improve the egg production rate. The present invention can be used in the early breeding stage to select the poultry with the required egg production rate, and therefore improve the rate of egg production.

DESCRIPTION OF THE PRIOR ART

As the production technology has improved and the demand for high quality meat product has increased over the recent years, the development of the livestock industry in Taiwan has gradually transitioned from regional based operations to finance and technology oriented enterprise operations. According to statistics, domestic livestock product amounts to approximately 30% of the production value in the agricultural industry over the recent years. The annual production value of the poultry industry is roughly $40 billion NTD, being the third largest industry in the agricultural business, only next to pigs and rice. Taiwan became a member of the World Trade Organization in 2001, and the current import of poultry product is based on tariff quota. As the cost of breeding poultry domestically is greater than that of European countries and America, after the announcement of full access to trade market in 2005, the domestic poultry industry has suffered a severe blow. At present, other than establishing effective distribution channels and improving the automated production techniques to lower the costs, increasing the reproductive capacity of poultry has also became an important challenge in order to raise the competitiveness of the agricultural industry.

Currently, the major focus in the poultry industry is on chickens, including broilers, chicken eggs and other related industries, wherein the annual production value of the broiler market is roughly $26 billion NTD, which amounts to 60% of the production value in the poultry industry. As there are no pure breed chicken in Taiwan, all the existing breeds are mixed-breeds of chickens introduced from Japan, southern China and other countries. However, without a systematized marker assisted selection method for reproduction, the reproductive capacity of these mixed-breeds has gradually decreased. The traditional mix-breeding technique of increasing reproductive capacity by improving the genetic characters no longer satisfies the demands of the existing condition due to its cost and the amount of time required.

Moreover, egg-laying ability is the main economic characteristic of poultry. In order to improve the egg-laying ability, poultry industries all over the world have implemented systematic breeding techniques, and are employing poultry bio-indicators such as body weight, growth period, rate of egg production, size of laid eggs, inter- and intra-clutches and hierarchical follicles etc., as considerations for improving the reproduction capacity and egg-laying ability. However, the related considering parameters: phenotype characteristics and traits of the egg-laying ability mentioned above are usually limited to mature female poultry only. Yet the breeding of certain poultry are not suited to known systematic breeding techniques. In recent years, there are many reports that indicate variations in the genotypes of functional genomics will influence the variations in phenotypes. Also, researches in genotypes and polymorphisms are now an important method for speeding up the researches regarding trait genes of poultry groups. Generally speaking, the above mentioned genetic researches are only limited to long term poultry breeding industry, and are not suited for random poultry breeding industry.

On the other hand, there are many variables which would influence the traits from avian sexual maturity to laying eggs and the egg production rate; these variables can be separated into external variables and internal variables. External variables include breeding environments and breeding methods, while internal variables include genetic characters and physiological regulations. Other than genetic characters, the external variables are usually very closely linked to the internal physiological changes. At present, the common methods used by chicken breeders are to utilize light irradiation time and nutrients to control egg-laying. Researches in light irradiation discovered that by shining visible light on birds, avian sexual maturity may be stimulated and lay eggs ahead of time. However, if complete nutrition needs are not met during poultry's egg-laying periods and the early stages, the quality of laid eggs would be poor even though the number of laid eggs has been raised. The increased number of eggs laid may be due to premature eggs or prolonged egg-laying periods, even though it is still uncertain which variables are related to egg production rates and broodiness, both premature eggs and prolonged egg-laying periods are all affected by the interrelation between the environment and the hormones, the hormones in each of the cell membrane protein receiver might play a more important role.

Currently, the country chicken genome research plan in Taiwan has conducted researches with the focus on the distinctive genes performance of selected high yield country chickens. Due to the low egg production rate, the cost for country chicken industry stays too high and gradually lowering the competitiveness, therefore, it is with hope that via researches in functional genomics and high yield genes would help to understand the performance of the genes within each tissue of the high yield country chickens (via expressed sequence tag research technique), and to research and develop genes that are related to the high yield characteristics (through suppression subtraction hybridization technique), thus understand and overcome the low yield problem of country chickens.

As the gene mapping of chicken is almost fully solved, the number of identified genes in gene mapping is also increasing. Furthermore, as the human genome information becomes gradually unraveled, the trend for biotechnology development will advance into post-genomic era, the biomarker development strategies with the focus on genomes and proteomes have gradually became the new mainstream for animal breeding technology. In order to increase the egg-laying ability of poultry, utilizing proteomics methods to increase the number of eggs laid or egg production rate have also became a new option. In the researches carried out by overseas academics, multiple types of development related proteins during the poultry growth process have been discovered, the performance of these proteins can be used as molecular markers for selecting the egg-laying ability. Currently, the breeding industry in Taiwan still lacks a systematized breeding method to increase the egg-laying ability of poultry; hence, in addition to breeding efficiency being lowered, the cost for breeding also increased relatively. Therefore, raising the egg production rate is an important challenge to stimulate the competitiveness of the breeding market.

Presently, at the country chicken market in Taiwan, the weekly output of the red-feathered country chicken is approximately 1.5 million units, the weekly output of the black-feathered country chicken is approximately 1 million units, therefore, and the total weekly output of Taiwan's country chicken market is roughly 2.5 million units. From the perspective of the country chicken market in Taiwan, the market demand is relatively high. Furthermore, traditional country chicken breeding techniques require roughly 40 weeks to forecast the egg production rate, which is very time consuming and inefficient. Due to the above, a method to raise the egg production rate while shortening the breeding time to match the high market demand is urgently needed.

For this reason, the present invention provides a poultry selection method, which utilizes the advantages of the protein analysis method and analyze the concentrations of specific serum proteins, and based on the egg production rate, selects the poultry as required in order to provide a reference base for the poultry industry and breeding researchers to improve the production rate of poultry, and provide a technique for scientific researches and industry applications.

SUMMARY OF THE INVENTION

The present invention will describe in detail some preferred embodiments. However, it should be noted that other than these detailed descriptions, the present invention can be practiced in a wider range of other embodiments besides those explicitly described, and the scope of the present invention is not expressly limited except as specified in the accompanying claims.

The object of the present invention is to provide a poultry selection method, for separating poultry with different egg production rates during different breeding stages.

Another object of the present invention is to provide a poultry selection method, where by using this selection method to select the poultry with the required egg production rate, hence, raise the egg production rate.

Yet another object of the present invention is to provide a poultry selection method, for eliminating low yield poultry at the early breeding stage, and improve the problem of low egg production rate in existing breeding techniques.

Yet another object of the present invention is to provide a poultry selection method, for raising the economic efficiency of poultry breeding industries in Taiwan and improving the market share.

The present invention discloses a poultry selection method to improve the egg production rate comprising: collecting protein samples with related quantity, concentration and egg productivity information from multiple poultry groups; transforming these protein sample concentration into multiple ratings (such as scores or levels), and create codes that correspond to these ratings; transforming protein sample quantity into multiple ranks, and create codes that correspond to these ranks; from multiple ratings, determine the tendency of multiple ratings; determine the required selection region based on the tendency of multiple ratings and the egg production information, and combine ratings' (such as scores) codes with ranks' codes to form the regional codes; compare the regional codes to determine the code matching rate of multiple groups; and based on the matching rate to select the poultry with the required egg production rate.

The present invention also discloses a poultry selection method to improve the egg production rate, comprising: the collection and ranking of protein samples and the related egg production information of known and unknown poultry groups to sort out the ratings; select a poultry group having the required egg production from the known group; define regional codes based on the ratings of the known group; compare the ratings between known and unknown groups, and select the poultry (from the unknown group) with the same regional codes to the previously selected poultry group with the required egg production; and select the poultry with the required egg production according to the matching rate after the comparison.

BRIEF DESCRIPTION OF THE DRAWINGS

The above objects, and other features and advantages of the present invention will become more apparent after reading the following detailed descriptions when taken in conjunction with the drawings, in which:

FIG. 2 illustrates the flowchart diagram outlining the steps for utilizing the poultry selection method to improve the egg production rate according to Embodiment 2 of the present invention;

FIG. 3 illustrates the serum protein concentration related information for the poultry with the lowest 20% in egg production in batch B poultry of the present invention;

FIG. 4 illustrates the serum protein levels related information according to batch A poultry of the present invention;

FIG. 6 illustrates the mean value analysis of the serum proteins within the two batches of poultry samples according to the present invention;

FIG. 7 illustrates the statistical analysis of the protein quantification for different breeding cycles according to the present invention;

FIG. 8A illustrates the statistical analysis of the selection values for the poultry with the lowest 20% in egg production within the different batches according to Embodiment 1 of the present invention;

FIG. 8B illustrates the statistical analysis of the selection values for the poultry with the lowest 20% in egg production within the different batches according to Embodiment 2 of the present invention;

DESCRIPTION OF THE PREFERRED EMBODIMENT

Figure 1:
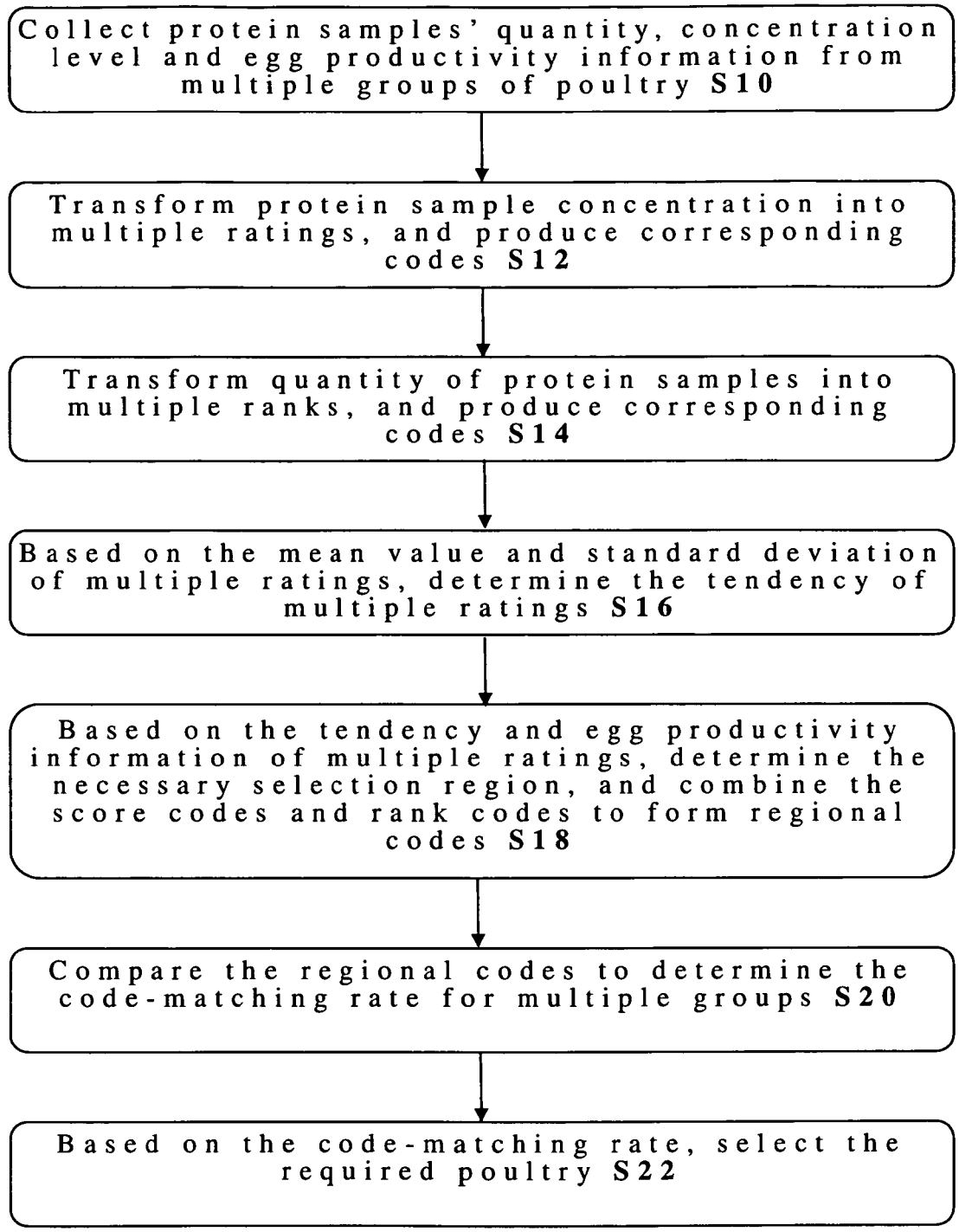
FIG. 1 illustrates the flowchart diagram outlining the steps for utilizing the poultry selection method to improve the egg production rate according to Embodiment 1 of the present invention.

In the following description, various specific details are provided in order to give a thorough understanding of the embodiments of the invention. The present invention is described in detail below, along with the preferred embodiments and accompanying drawings, it should be recognized that all the preferred embodiments are for the purpose of illustration only, and not for the purpose of limiting the present invention. Those skilled in the art will recognize that the invention may be practiced without one or more of the specific details, or with other methods, components, materials, etc.

The present invention uses the Taiwan red-feathered country chicken (TRFCC) as a preferred embodiment, and as explained below, TRFCCs with different breeding cycles are employed. It should be recognized that TRFCC is considered as the research objective to illustrate the embodiment of the present invention, and is not to be used to limit the scope of the present invention.

Collection of Poultry Samples

Two different batches of poultry samples have been selected from the TRFCCs in a poultry breeding farm in southern Taiwan, these two batches are categorized into batch A (hatched in June 2003) and batch B (hatched in September 2003). Each batch of poultry is to be bred until 21 weeks old, while maintaining moderate body weight. By week 22, all the poultry would be photostimulated, and the laying cycle is maintained at 30 weeks. The photostimulation cycle includes the transition from the cycle of 8 hours illumination and 16 hours darkness to the cycle of 16.5 hours illumination and 7.5 hours darkness. Each day, the total amount of eggs laid is recorded individually until 25-48 weeks of age.

Serum samples are collected from the two batches of poultry, then, for 2 hours, these samples are kept under room temperature to permit clot formation, after the clot formation, these samples are then operated in a centrifuge with the gravity of 1000×g for 20 minutes. Using the bovine serum albumin as the standard, by utilizing the Bradford method (as published by Lopez et al. in Clin. Chim. Acta. Vol. 220 Pg. 91-100, 1993, "An improved Bradford protein assay for collagen proteins") to perform quantified analysis on serum proteins. Then, each protein sample is portioned evenly and stored at the temperature of −70° C. for subsequent analysis.

Analysis of Protein Profiles—Polyacrylamide Gel Electrophoresis (PAGE)

The samples are prepared for sodium dodecyl sulfate polyacrylamide gel electrophoresis (SDS-PAGE) analysis. As SDS-PAGE analysis is a well known protein analysis method to those skilled in the art, hence, unnecessary details will not be described.

Each sample is separated on a 14.5% resolving gel and stained with the Coomassie blue solution (obtained via dissolving 0.025% Coomassie blue in 10% acetic acid). After that, a laser densitometer (Amersham Bioscience) is used to analyze the required protein bands, and saved it as Tiff image files.

Within the serum samples of the high egg production group, proteins that are related to egg production rates, such as vitellogenin, apolipoprotein A-I, apo-VLDL-II are normalized. And through the use of matrix-assisted laser desorption ionization time of flight mass spectrometry (MALDI-TOF MS) to define the identity of the protein, for a detailed description of the steps involved, please refer to "Fast-response proteomics by accelerated in-gel digestion of proteins" as published by Havlis et al. in Anal. Chem. Vol. 75 Pg. 100-106, 2003.

Analysis of X Protein Levels

Protein chip technology is used to evaluate the level of serum protein concentration. Then, an automated peptide synthesizer (Symphony multiple Synthesizer) is used along with a Multiple Antigen Peptide (MAP) system (as published by Tam and Zavala in J. Immunol. Methods Vol. 124 Pg. 53-61, 1989, "Multiple antigen peptide. A novel approach to increase detection sensitivity of synthetic peptides in solid-phase immunoassays") to synthesize a synthetic peptide corresponding to codons 75 to 89 (KPTGYGSSSRRLHHK) of the poultry Insulin-like Growth Factor-I (IGF-I) gene (as published by Kajimoto and Rotwein in Mol. Endocrinol. Vol. 3 Pg. 1907-1913, 1989, "Structure and expression of a chicken insulin-like growth factor-I precursor"). The peptide is used to immunize rabbits to produce a polyclonal antiserum against the IGF-I epitope.

During the protein chip preparation, the robotic microarrayer of the spray type spots the crude sera in an ordered array onto the nitrocellulose membrane, where the distance between each slide is 1500 μm. Then, Tris-Tween Buffered Saline (TTBS) solution (20 mM Tris. HCl (pH 7.5), 500 mM NaCl and 0.5% Tween-20) is used to rinse the nitrocellulose membrane in order to remove any unbounded proteins. The protein chip is immersed in TTBS solution containing 3% skim milk, to block unreacted sites for one hour under room temperature, and washed three times with the TTBS solution (washing buffer).

The prepared protein chips are incubated with the IGF-I peptide-immunized polyclonal antiserum for one hour, and washed three times with washing buffer. After that, they are incubated with the anti-rabbit antibody conjugated to alkaline phosphatase (Sigma, St. Louis, Mo., USA) for one hour, and stained with nitro blue tetrazolium and 5-bromo-4-chloro-3-indolyl phosphate. Finally, laser densitometer is used to analyze the required protein spots and save the images as Tiff files. Normalized analysis is performed on the relative level of X protein against the serum concentration of 35 weeks old poultry.

Statistical Analysis

Through the utilization of Student's t test, the serum protein levels at 14, 24 and 35 weeks of age within the two batches of poultry are analyzed. In addition, the associations between the protein levels of TRFCCs at 14, 24 and 35 weeks of age and the overall number of eggs produced are analyzed.

Correlation analysis is used to determine the correlation coefficient between the overall egg production and the serum protein level. Moreover, all the statistical analyses are performed using the SPSS software version 11.5 (SPSS Inc., Chicago, Ill., USA), and $p<0.05$ is considered significant.

Embodiment 1

Selection Method

Two different batches (batch A and batch B) of TRFCCs raised in different seasons are used for selection. As the mean serum protein levels and the overall egg production between the two different batches are different, hence, the traditional statistical analysis method of using the serum protein as the selection method can not be applied for poultry selection. Therefore, the present invention provides a novel selection method termed code-selection approach, to solve the above mentioned problem.

In the present invention, the batch of poultry with low egg production records is used as the training set to select poultry in another batch. The serum protein levels are transformed into a set of ratings, such as scores and ranks, and the scores and ranks are then combined to form regional codes. Within the two different batches, the poultry with 100% or 75% codes-matches are selected. The details are described below.

The present invention utilizes information related to serum proteins and egg production rates of the known batch B poultry to evaluate the egg production rate of batch A poultry and also perform selection within batch A poultry.

The total number of poultry for batch A and batch B are m and n respectively, each poultry is randomly given a poultry number, and the total egg production throughout the life of batch B poultry is given as E. A total number of poultry (in this case, the total number for batch B poultry, n) is selected as the individual poultry in each batch. x is used as the selection parameter for a type of serum protein. The relative serum concentration of proteins in the individual poultry is represented as a score. If four types of serum proteins are selected, then four scores would be obtained.

After that, the codes for the two batches are transformed into a set of scores. The steps involved are described below.

Step 1:

The scores for the two batches of poultry are ranked, and each score corresponds to a rank. Therefore, each poultry is given a set of ranks. Please refer to FIG. 3, where the poultry with the lowest 20% in egg production in batch B (n=14) are selected first, in order to search for identical ranks in both batches of poultry. Then, the selected poultry in batch B are used as the training set, for the selection of low egg production poultry in batch A, please refer to FIG. 4.

Step 2:

As the numbers of poultry in the two batches are different, the ranks of batch A poultry are transformed to correspond to batch B poultry. Therefore, after the transformation, the ranks for batch A are represented as $RB_t$.

$$R_{B_t} = R_{A_i}\left(\frac{n}{m}\right)$$

Wherein, $R_{Ai}$ represents the i rank in batch A, $R_{Bt}$ represents the ranks after encoding, please refer to FIG. 4. When the numbers of TRFCCs in the two batches are different, it is impossible to find the poultry with the same rank in the two batches, thus the ranks for batch A need to be transformed. The ranks for the post-transformation batch A that are close to the ranks for batch B are selected.

Step 3:

As the mean concentrations of poultry serum proteins for the two batches are different, the tendency of the poultry scores is observed. The ith poultry score is transformed into $T_{Bii}$, please refer to FIG. 4.

$$T_{Bi} = (T_{Ai} - \overline{X_A})s_B/s_A + \overline{X_B}$$

Wherein, $T_{Ai}$ represents the score of ith poultry within batch A, $\overline{X_A}$ and $\overline{X_B}$ represent the mean score for batch A and batch B respectively, whereas $S_A$ and $S_B$ represent the standard deviation for batch A and batch B.

Step 4:

Due to the difference of scores between the two batches ($T_{Bti}$ and $T_{Bti+1}$), the score within batch A poultry that is close to $T_{Bi}$ (refer to FIG. 3) is selected first. As the margin of error from $T_{Bi}$ to nearby scores, $T_{Bti}$ and $T_{Bti+1}$ is inconsistent, the error distance can be further adjusted. In order to adjust the distance between $T_{Bi}$ and its nearby scores $T_{Bti}$ and $T_{Bti+1}$, such that they are evenly spaced, the score with a larger headway is selected. $T_{Bi}$ is regarded as the score for batch B, if $|T_{B_i} - T_{B_{t\,i}}| < |T_{B_{t\,i+1}} - T_{B_i}|$, then the selected distance d is defined as $T_{B_i} - |T_{B_{ti+1}} - T_{B_i}| < d < T_{B_{t\,i+1}}$.

Step 5:

According to steps 2 and 4, the selected ranks and scores would form several selected regions. These regions are arranged into ranks, and each selected region within the ranks and scores would attain a code. By combining the codes for ranks and-scores, then each poultry would attain a regional code. For example, if both the ranks and scores for Poultry No. 3 are 6.1.1.1, then the regional code would be 6.1.1.1 Therefore, each poultry is able to obtain a code defined by ranks and scores.

When the ranks and scores for the poultry are different, then the regional codes are adjusted to include two codes. For example, if the ranks and scores for Poultry No. 45 are 1.2.4.7 and 1.2.3.7 respectively, then the regional code would be 1.2.4/3.7.

Step 6:

According to the selected region, each poultry in batch A of TRFCC also include a set of regional codes. However, when the ranks and scores of poultry do not lie within the selected regions, then the regional codes are re-encoded according to the following aspects. Firstly, when the codes do lie within the selected regions, the regional codes of the poultry that is closer to the original regional codes are selected, to adjust the original regional codes. Subsequently, when the codes do not lie within the selected regions, then the codes are encoded through linear interpolation.

When the regional codes for batch A poultry is a match with the codes of the selected region, then it is termed 100% code-match. However, when the value of the code lies within the range of mean±standard deviation, then code±1 is used to encode any of the two codes within the regional code. If the regional codes for the batch A poultry is a match with the codes of the selected region after the encoding process (code±1), then it is termed 75% code-match. For example, the regional code of Poultry No. 78 in batch A is 6.1.2.1, which is a match with the regional code 6.1.1/2.1 for Poultry No. 36 in batch B. Therefore, 100% code-match poultry can be selected.

Step 7:

The overall egg production for the A batch poultry is ranked, and the poultry with the lowest 20% or 50% in egg production are selected. The number of the correctly selected poultry is divided by the number of selected poultry, to calculate the accuracy of the selection values within the A batch poultry. In addition, prediction rate is defined as the percentage of selection values.

Step 8:

The poultry with 75% code match are selected at phase one (14 weeks), phase two (14 and 24 weeks), and phase three (14, 24 and 35 weeks) of the breeding stages, and the egg production rates are calculated.

Embodiment 2

Selection Method

From another perspective of the present invention, the present invention also provides a statistical method to select the poultry with improved egg production, this method takes the related serum protein values of the different batches of poultry and utilizes simple statistical methods for calculation, and the required poultry is selected according to the results of the calculation, detailed steps are described below.

The preprocessing methods are as follows: (1) the four proteins and egg productivity information E (egg variable) in the batches of reference group B is collected, each protein has a score $B-x_j^m$. The scores $B-x_j^m$ are then ranked according to the values of $B-x_j^m$, to obtain vector $B-s_k^m$. The egg productivity information E are ranked, and the lower set is used as the training set, and the score $B-ek_e^m$ is produced, wherein e=1, 2, ..., $cn_B$. The training set is then ranked to produce vector $B-er_e^m$. (2) the four protein information in the batches of experimental group A is collected, each protein has a score $A-x_i^m$. The scores $A-x_i^m$ are ranked according to the values of $A-x_i^m$, to obtain vector $A-s_r^m$.

The selection analysis method is as follows: the poultry number m within the A batch equals $1, 2, \ldots, p(I)$, $$\text{when } n_A \neq n_B, e=1, 2, \ldots, cn_B \quad (II)$$

$$\begin{cases} B\text{-}RT_e^m = \dfrac{B - ek_e^m * n_A}{n_B} \\ B\text{-}NRT_e^m = \lfloor RT_e^m \rfloor \\ B\text{-}ST_e^m = \dfrac{(B\text{-}er_e^m - \text{mean}(B\text{-}s_\cdot^m)) * S.D.(A\text{-}s_\cdot^m)}{S.D.(B\text{-}s_\cdot^m)} + \text{mean}(A\text{-}s_\cdot^m) \end{cases}$$

Based on $$B\text{-}RT_k^m = \dfrac{B\text{-}s_k^m * n_A}{n_B},$$

transform the $B\text{-}s_k^m$ of the training set; and based on $$B\text{-}ST_j^m = \dfrac{(B\text{-}x_j^m - \text{mean}(B\text{-}x_\cdot^m)) * S.D.(A\text{-}x_\cdot^m)}{S.D.(B\text{-}x_\cdot^m)} + \text{mean}(A\text{-}m_\cdot^m),$$

transform $B\text{-}x_j^m$, wherein the mean and standard deviation of reference group B are represented by $\text{mean}(B\text{-}x^m.)$ and $S.D.(B\text{-}x^m.)$ respectively, and the mean and standard deviation of experimental group A are represented by $\text{mean}(A\text{-}x^m.)$ and $S.D.(A\text{-}x^m.)$ respectively.

The selection statistical method of the present invention is as follow:

if $B\text{-}ST_e^m \geq A - s_{B\text{-}NRT_e^m}^m$ and $A\text{-}s_{B\text{-}NRT_e^m}^m > A\text{-}s_{up_{e-1}}^m$, (1)

then $\text{low}_e = B\text{-}NRT_e^m$, when $i = \text{low}_e$ to $A\text{-}s_i^m > B\text{-}ST_e^m$, $$\begin{cases} A\text{-}RF_i^m = e - w + 1; \\ i++. \end{cases}$$

$up_e = i; \quad B\text{-}RF_e^m = e - w + 1.$ if $B\text{-}ST_e^m < A - s_{B\text{-}NRT_e^m}^m$ and $A\text{-}s_{B\text{-}NRT_e^m}^m > A\text{-}s_{up_{e-1}}^m$, (2)

then $up_e = B\text{-}NRT_e^m$, when $i = up_e$ to $A\text{-}s_i^m < B\text{-}ST_e^m$, $$\begin{cases} A\text{-}RF_i^m = e - w + 1; \\ i--. \end{cases}$$

$\text{low}_e = i; \quad B\text{-}RF_e^m = e - w + 1.$ if $B\text{-}ST_e^m \geq A - s_{B\text{-}NRT_e^m}^m$ and $A\text{-}s_{B\text{-}NRT_e^m}^m \leq A\text{-}s_{up_{e-1}}^m$, (3)

then $\text{low}_e = up_{e-1}$, when $i = \text{low}_e$ to $A\text{-}s_i^m > B\text{-}ST_e^m$, $$\begin{cases} A - RF_i^m = e - w; \\ i++ \end{cases},$$

$up_e = i; \quad B\text{-}RF_e^m = e - w; w++.$ if $B\text{-}ST_e^m < A - s_{B\text{-}NRT_e^m}^m$ and $A\text{-}s_{B\text{-}NRT_e^m}^m \leq A\text{-}s_{up_{e-1}}^m$, (4)

then $\text{low}_e = up_{e-1}$, when $i = \text{low}_e$ to $A\text{-}s_i^m > A - s_{B\text{-}NRT_e^m}^m$, $$\begin{cases} A\text{-}RF_i^m = e - w; \\ i++ \end{cases},$$

$up_e = i; \quad B\text{-}RF_e^m = e - w; w++.$

Binary search is then employed to find out $A\text{-}RF_i^m = B\text{-}RF_e^m$, wherein $m = 1, 2, \ldots, p$.

For each protein, the regional codes are found within experimental group A based on $B\text{-}RT_j^m$ and $B\text{-}ST_j^m$ of each poultry in the training set. In other words, the $B\text{-}RT_j^m$ value and $B\text{-}ST_j^m$ value of the first poultry within the training set are selected first, and used as the standard value for the defined regional codes; other poultry are then found within experimental group A, and the $A\text{-}x_i^m$ value and $A\text{-}s_i^m$ value of these poultry need to fulfill one of the following situations. First situation: when $A\text{-}x_i^m \leq B\text{-}ST_k^m$ and $A\text{-}s_j^m \geq B\text{-}RT_k^m$ or another situation: when $A\text{-}x_i^m \geq B\text{-}ST_k^m$ and $A\text{-}s_j^m \leq B\text{-}RT_k^m$, if any of the above situations is fulfilled, then the regional code of this poultry in training set B and the regional code of the poultry found in experimental group A are defined as 1. Based on the same principle, the $B\text{-}RT_j^m$ value and $B\text{-}ST_j^m$ value of another poultry are selected from the training set, and used as the standard value for the next defined regional codes, until each poultry within the training set is selected. While these steps are being carried out, if different regional codes are found to include the same poultry, then priority is given to the regional code that has appeared first. According to the above, each poultry within the training set has a set of regional codes, and each poultry within experimental group A also has a set of regional codes or non-regional codes. If a set of regional codes in experimental group A is the same as the regional codes of the training set, then it can be hypothesized that this poultry in experimental group A is a low egg production poultry.

Selection Results and Analysis

Egg Production Rates

The overall egg productions during the 25 to 48 weeks period are recorded for the two batches of poultry. Even though the poultry are bred at the same farm, the timings for cultivation are different and seemed to reflect on the rates of egg production. As there is a 3 month difference between the hatching times of the two batches of poultry, the peak egg production period (after 30-40 weeks of breeding) for batch A and batch B is roughly at February to April, and April to June, respectively.

Using SDS-PAGE and MALDI-TOF to Analyze Serum Protein

The present invention utilizes the egg production related protein to perform the analysis. 9% resolving gels are used to analyze the difference in performance for the serum proteins vitellogenin (~200 kDA) and apo A-I (~25 kDa) between the highest egg producing poultry and lowest egg producing poultry among the TRFCCs. As the more important biomarkers are usually proteins and peptides with lower molecular weights, therefore, 14.5% separating gels are used to evaluate the performance of the serum protein for the poultry that has been bred for 35 weeks. The major protein bands within the serum protein can be differentiated through SDS-PAGE. Via MALDI-TOF MS, proteins that are close to 200 kDa and 25 kDa are defined as vitellogenin and apo A-I respectively, while the protein (P10) that is close to 10 kDa is defined as apo VLDL-II (very low density lipoprotein-II).

According to "Apolipoprotein VLDL-II inhibits lipolysis of triglyceride-rich lipoproteins in the laying hen" published by Schneider et al. in J. Lipid Res. Vol. 31 Pg. 507-513, 1990, the role of the apo VLDL-II is to transport the VLDL from the liver to the oocyte through the plasma. The literature "Amino acid sequence of a major apoprotein from hen plasma very low density lipoproteins" published by Jackson et al. in J. Biol. Chem. Vol. 252 Pg. 250-253, 1977, has discovered that the apo VLDL-II protein can be found inside the plasma and it contains two identical polypeptide chains of 82 amino acids and its molecular weight is approximately 9.3 kDa. According to "Plasma apolipoprotein VLDL-II and egg production in laying hens: establishment of an ELISA method" published by Pinchasov Y. et al. in Reprod. Nutr. Dev. Vol. 34 Pg. 361-369, 1994, it has been discovered that the concentration of apo VLDL-II is related to the egg production ability, and that the high egg production poultry would show a higher concentration of apo VLDL-II.

Statistical Analysis of Serum Protein Concentration and Egg Numbers in TRFCC

According to "Seasonal variation in plasma lipids, lipoproteins, apolipoprotein A-I and vitellogenin in the freshwater turtle" published by Duggan et al. in Comp. Biochem. Physiol. A Mol. Integer. Physiol. Vol. 130 Pg. 253-269, 2001, it has been suggested that the performance of lipid, lipoprotein, apolipoprotein A-I and vitellogenin in the freshwater turtle Chrysemys picta would change due to seasonal variations. The literature named "Age-related, sex-related and seasonal changes of plasma lipoprotein concentrations in trout" published by Wallaert and Babin in J. Lipid Res. Vol. 35 Pg. 1619-1633, has pointed out that the lipoprotein concentration within the plasma of trout would vary with age, sex and season. According to the two research literatures mentioned, the serum protein concentration would fluctuate, depending on the environment and endogenous biological rhythm.

Referring to FIG. 6, in order to study the variations in the serum protein for the two batches of poultry, the mean concentration of serum protein in 14, 24 and 35 weeks old poultry need to be determined first. In the two batches of poultry, the mean concentration of apo A-I and X protein at the premature phase (14 weeks, $p<0.001$) and the initial egg production phase (24 weeks, $p<0.001$) are obviously different. Furthermore, the mean concentration of apo VLDL-II in the two batches of poultry is also different to that of the egg production periods (24 weeks, $p=0.027$; 35 weeks, $p=0.003$). And the mean concentration of vitellogenin in the two batches of poultry is also different to that of the peak egg production period (35 weeks, $p=0.000$). Therefore, it can be perceived that the environment and the endogenous biological rhythm would change the serum protein concentration.

Furthermore, the concentration levels for the three types of serum proteins (apo VLDL-II, X protein and vitellogenin) would gradually increase at the initial egg production phase, and then greatly increase at the later period (35 weeks). On the other hand, the concentration level of serum protein apo A-I declines at the egg production period, as suggested by the literature "Alteration in plasma lipoproteins and apolipoproteins associated with estrogen-induced hyperlipidemia in the laying hen", published by Hermier et al. in Eur. J. Biochem. Vol. 184 Pg. 109-118, 1989.

According to the researches done in the present invention, notable increases in protein levels and overall egg production occurred during the peak egg production period (35 weeks, $p=0.000$), rather than the initial egg production phase (24 weeks). Therefore, multiple environmental variables can be eliminated. Researches carried out in the present invention have investigated whether correlations between protein levels and overall egg production in both batches of poultry remained in agreement. Results have shown that, within the two batches of poultry, the tendency of correlations between the protein levels and the overall egg production are slightly different. Within batch B poultry, levels of the four serum proteins have increased notably at the peak egg production period (35 weeks, $p=0.000$) compared to the premature period (14 weeks) and the initial egg production phase. However, within batch A poultry, the serum protein levels for apo VLDL-II and vitellogenin and overall egg production are not correlated to any of the three time periods mentioned (14, 24 and 35 weeks). Results have shown that the correlations between serum protein levels and overall egg production might be conditional and/or batch-dependent.

The Accuracy of Selection Values by Serum Protein Levels

As the mean concentration of serum proteins between the two batches are varied, the code selection approach is used to transform the serum levels into scores and ranks. Poultry with a 100% code-match or a 75% code-match are selected, as per FIG. 5. Due to the notable increase in serum protein concentration and egg production number for poultry at 35 weeks, the accuracy of the selection may reach 61.5-83.3%. In addition, in the early stages (14 weeks), a 100% code-match or a 75% code-match method can be used to select the poultry. Thus, the present invention provides an effective method to select poultry at the early stage of breeding.

Evaluation of Egg Production Rate by the Code-Selection Approach

Truncation selection is used to estimate the egg production rate of the 14, 24 and 35 weeks old poultry in batch A, as shown in FIG. 6. As a result of three-stage truncation selection, the rate of egg production has increased by 4% compared to the egg production rate for batch A, and the phase one (at 14 weeks) selection approach has increased the egg production rate by 3% compared to batch A. Therefore, the present invention is able to utilize the selection method to screen the low egg production poultry at the early stages of breeding (14 weeks), to increase the egg production rate.

According to one perspective of the present invention, the present invention provides a method of selecting poultry with different egg production rates during different breeding stages, the steps involved are described below. The protein samples of poultry during different breeding stages are collected first, for the preparation of protein samples and known markers. Then, protein separation and related analyses are performed on the protein samples and known markers. Then, from the results of protein separation and related analyses, the protein samples and its content are determined, and poultry with different egg production rates during different breeding stages are selected.

In the embodiment of the present invention, different breeding stages can range from birth to 48 weeks of age, the preferred poultry are 14, 24, 35 weeks old. The protein samples are serum proteins that are related to egg production rate, such as apo A-I, apo VLDL-II, X protein and vitellogenin. For the ease of performing separation analysis and related analyses on the protein samples, the known markers may be proteins' molecular weight marker. In one embodiment, the separation analysis and related analyses include:

electrophoresis, such as SDS-PAGE; protein mass spectra analysis, such as MALDI-TOF MS; and other types of statistical analysis methods.

According to one perspective of the present invention, the present invention also provides a poultry selection method to improve the egg production rate. FIG. 1 illustrates the flowchart diagram outlining the steps for utilizing the poultry selection method to improve the egg production rate according to Embodiment 1 of the present invention, the steps involved are described in detail below.

S10: collect protein samples' quantity, concentration level and egg productivity information from multiple groups of poultry. S12: transform protein sample concentration of multiple groups of poultry into multiple ratings (such as scores or levels), and produce codes that correspond to these ratings. S14: transform the quantity of protein samples into multiple ranks, and produce codes that correspond to these ranks. When the quantities of protein samples between multiple groups of poultry are different, the ratio of protein samples between multiple groups of poultry can be used for the transformation to obtain multiple ranks. Then, S16: based on the mean value and standard deviation of multiple ratings the tendency of multiple ratings is determined.

S18: from the tendency and egg productivity information of multiple ratings, determine the necessary selection region, and combine the rating (such as scores) codes and rank codes to form regional codes. When the multiple scores between multiple groups of poultry are different, the scores that are adjacent to the multiple scores can be used as the basis to help with the determination of selection region. S20: compare the regional codes to determine the code-matching rate for multiple groups. S22: based on the matching rate, select the poultry with the required egg production rate.

According to another perspective of the present invention, the present invention also provides another poultry selection method to improve the egg production rate. FIG. 2 illustrates the flowchart diagram outlining the steps for utilizing the poultry selection method to improve the egg production rate according to Embodiment 2 of the present invention, the steps involved are described in detail below.

S30: collecting and ranking the protein samples and the egg production rate information of known and unknown poultry groups to sort out the ratings. S32: select a poultry group with low egg production rate. S34: based on the ratings of known poultry groups to define the regional codes. S36: compare the ratings between known and unknown groups, and from the unknown groups, select the poultry with the same regional codes as the low egg production poultry. S38: select the poultry with the required egg production rate based on the comparison results of regional codes' matching rate.

FIG. 3 to FIG. 9 illustrate the analytical and statistical results obtained from the methods provided by the present invention. FIG. 3 illustrates the serum protein level related information for the poultry with the lowest 20% in egg production in batch B (35 weeks) poultry, including poultry numbers, overall egg production, and the scores and ranks for four types of serum proteins. FIG. 4 illustrates the serum protein levels related information according to batch A poultry, including poultry numbers, the scores and ranks for four types of serum proteins, and the scores and ranks after transformation.

Figure 5:
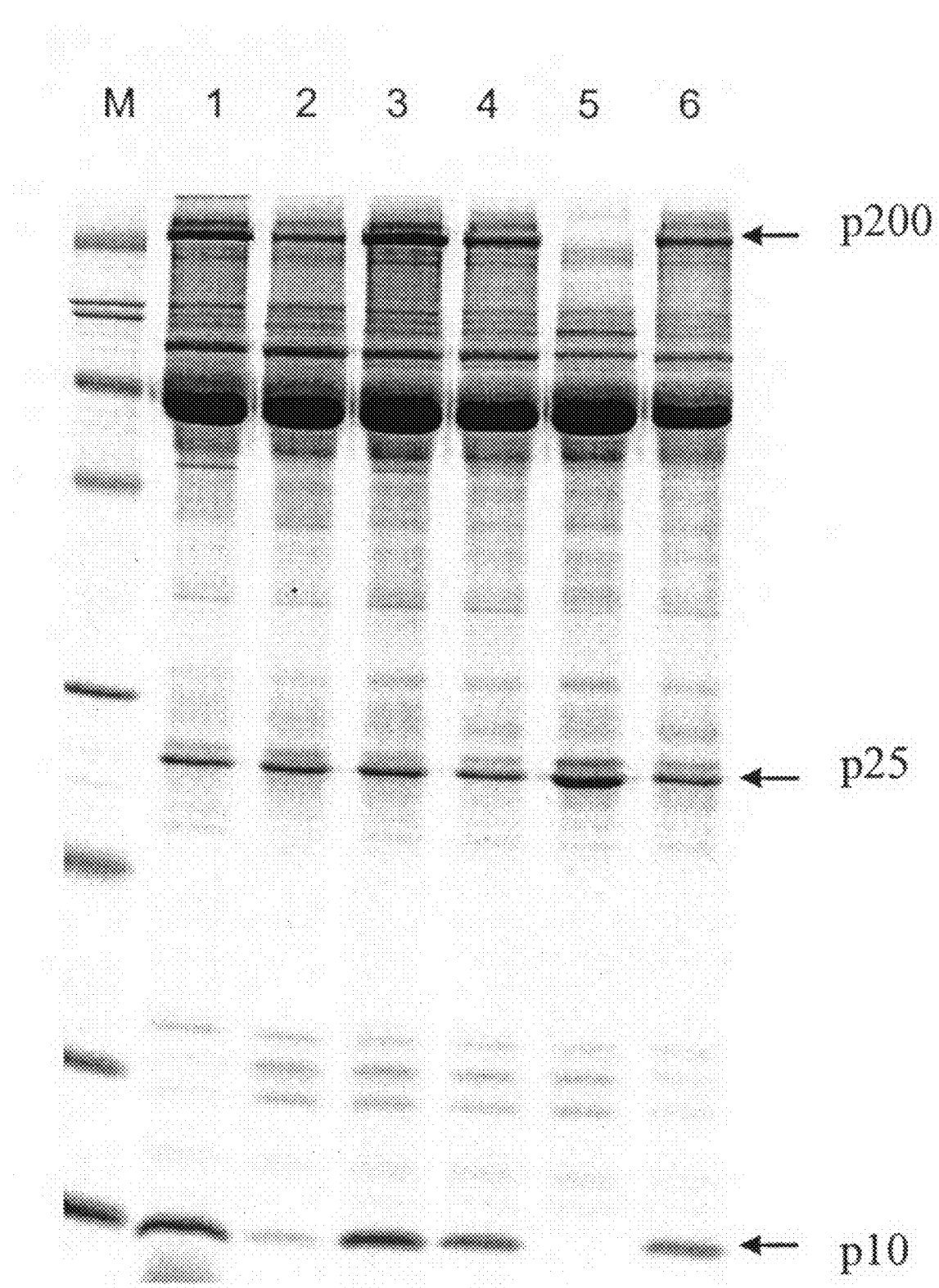
FIG. 5 illustrates the SDS-PAGE analysis diagram of the serum protein for poultry samples with different egg production rates according to the present invention.

FIG. 5 illustrates the serum protein SDS-PAGE analysis diagram of poultry samples with different egg production rates according to the present invention. The M shown on the PAGE represents the molecular weight markers used in the quantitative analysis, Lanes 1, 2, 3, 4, and 6 represent the serum samples of high egg production rate poultry, and Lane 5 represents the serum sample of low egg production rate poultry. The regions pointed out by the arrows in the diagram are the protein bands of serum proteins used in the present invention that are related to egg production ability, wherein p10 represents apo VLDL-II, p25 represents apo A-I, and p200 represents vitellogenin. It can be observed from the diagram that high egg production poultry show higher amounts of apo VLDL-II (p10) and vitellogenin (p200), while low egg production poultry show a higher amount of apo A-I (p25).

FIG. 6 illustrates the mean value analysis of the serum protein within the two batches of poultry samples according to the present invention. The diagram shows the serum protein level's statistical analysis for different breeding cycles (including 14, 24, and 35 weeks) of poultry in the A and B batch, including mean value, standard deviation, p value and degree of freedom. FIG. 7 illustrates the statistics related analysis of the protein quantifications of different breeding cycles according to the present invention.

Figure 9:
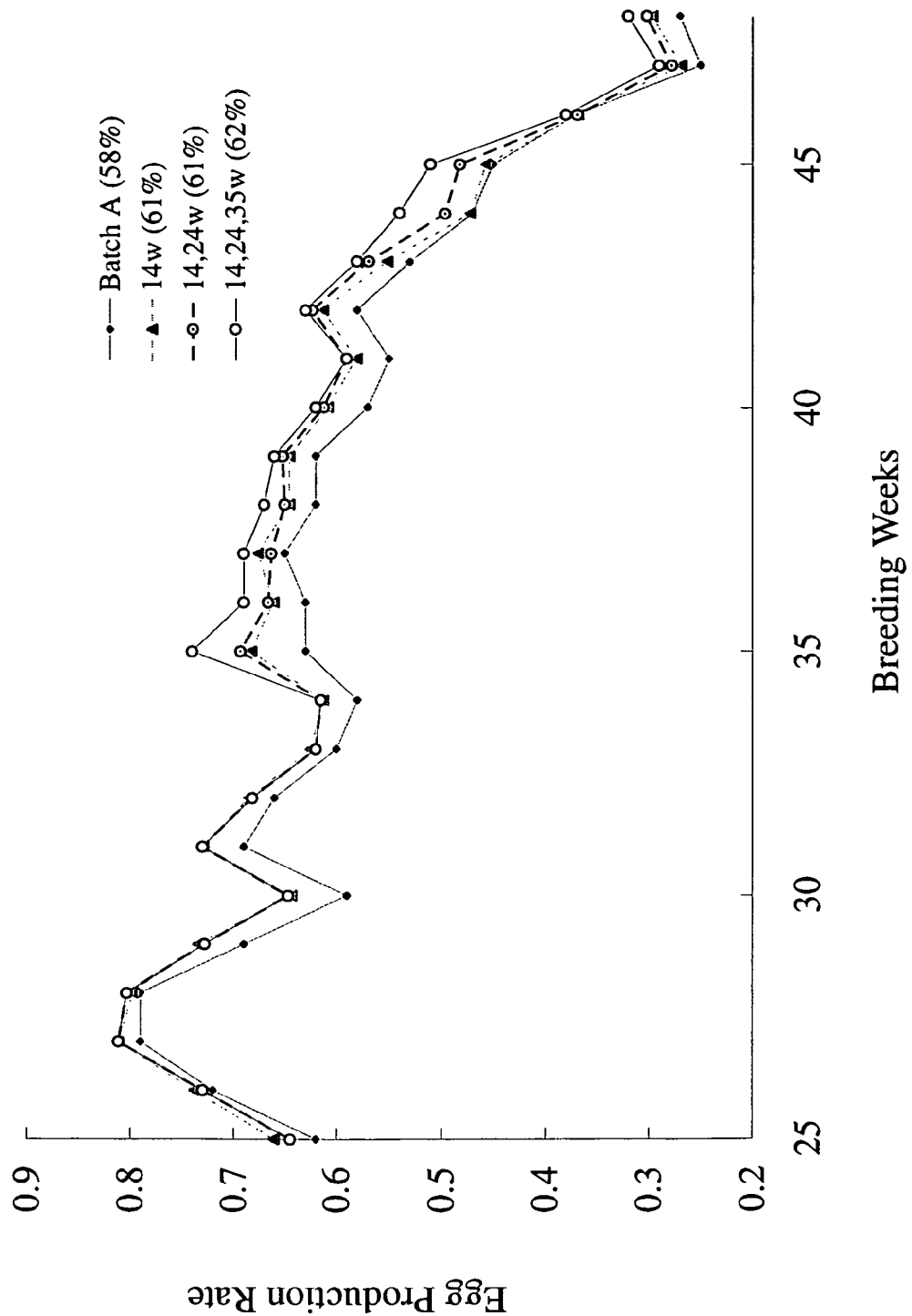
FIG. 9 illustrates the relationship diagram of the egg production rates for poultry at different weeks of age according to the present invention.

Referring to FIG. 8A and FIG. 8B, wherein FIG. 8A illustrates the analysis result of the selection comparisons for Embodiment 1, FIG. 8B illustrates the analysis result of the selection comparisons for Embodiment 2. Furthermore, * represents the selection values of batch A estimated by 20% or 50% of low egg production group in batch B, a represents the identical match of regional codes in batch A. FIG. 9 illustrates the relationship diagram of the egg production rates for poultry of different breeding ages according to the present invention.

Figure 10A:
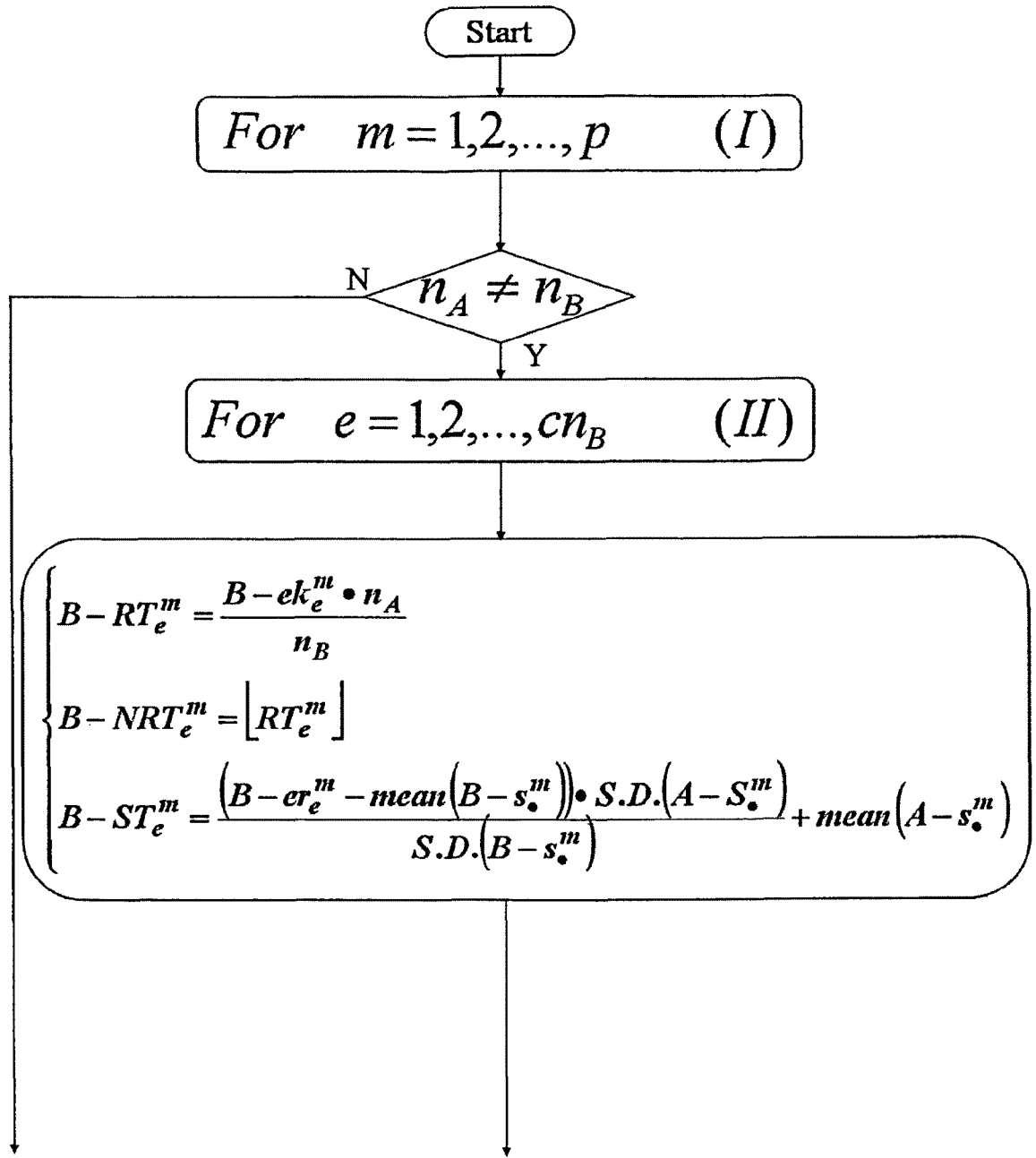
FIGS. 10A-10C illustrate the statistical analysis flowchart diagram of the selection method according to the present invention.
Figure 10B:
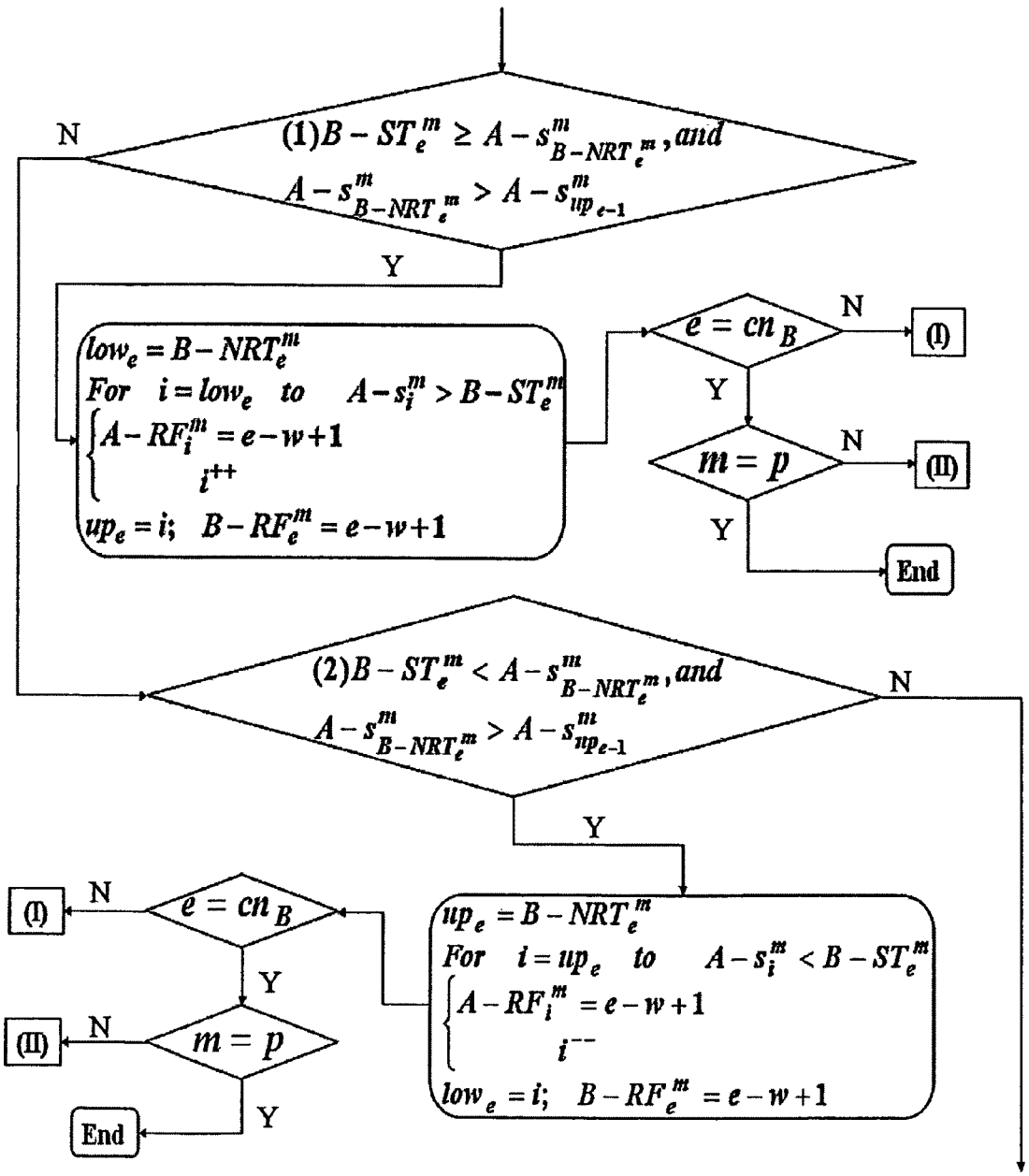
Figure 10C:
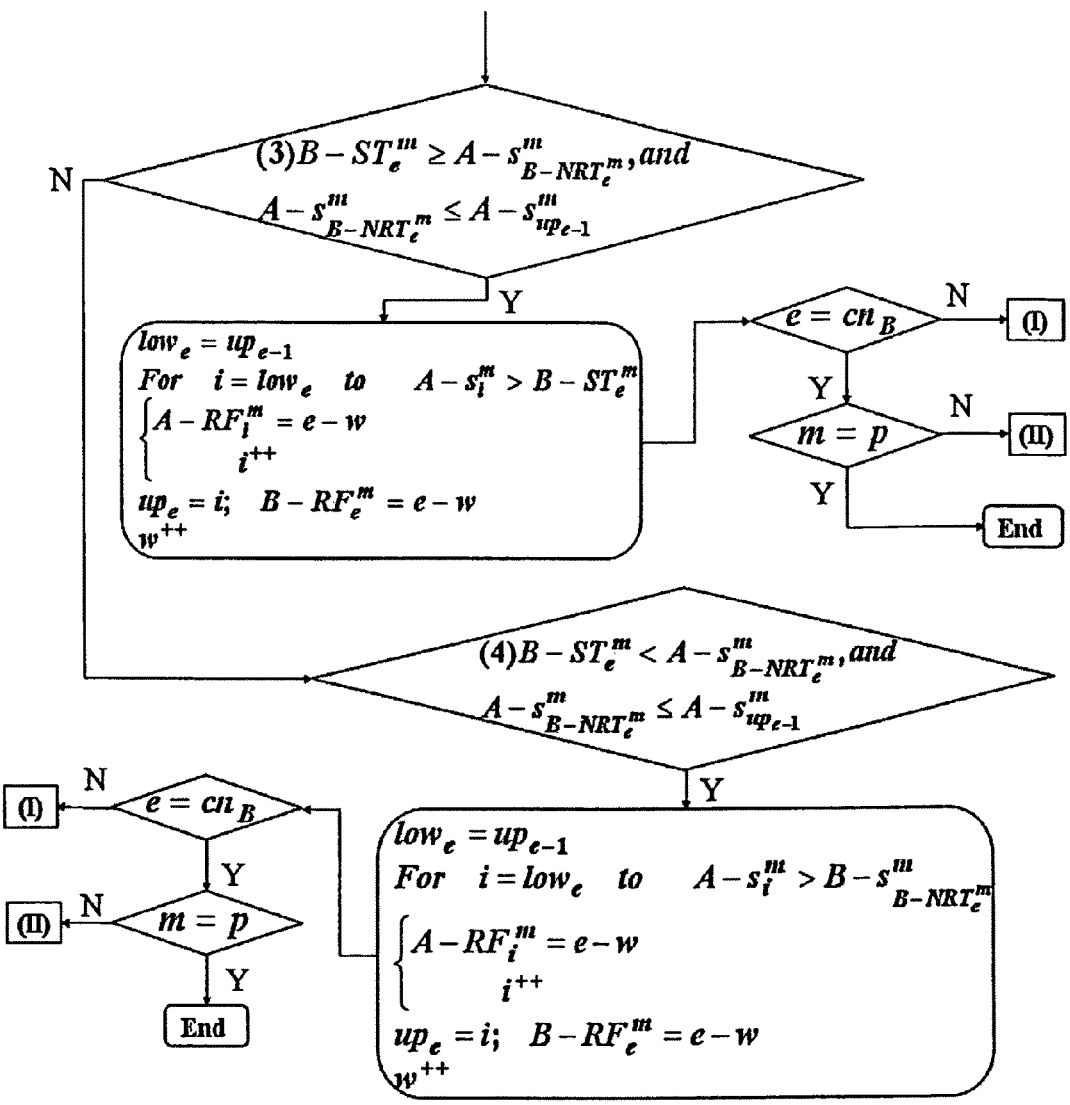

FIGS. 10A-10C illustrate the statistical analysis flowchart diagram of the selection method according to the present invention, wherein A and B represent different batches of poultry, nA and nB represents the quantity of batch A and batch B poultry respectively, e is the number of eggs produced, $cn_B$ is the number of eggs produced by batch B and may be set as the required ratio to be used as the training set, RT represents the normalization of ranks, ST represents the normalization of protein levels, mean represents the mean value, S.D. represents the standard deviation. In one embodiment, normalization is carried out through rounding the obtained value to the nearest whole number.

According to the methods and steps mentioned above, the present invention can establish a serum protein data group related to egg production rate, using this data group, the egg production rate status of the newly-bred unknown poultry can be evaluated. By transforming the collected serum proteins' related value data of unknown poultry into multiple ratings, such as scores and ranks, combining them into regional codes, and compare the regional codes to determine the matching rate, the required poultry can be selected.

In one embodiment, the poultry mentioned in the present invention comprises different types of egg-laying poultry including chickens, ducks, geese and birds.

From the analysis results, it can be seen that the present invention may be used at the early breeding stage to assess the poultry's egg production rate, and screen out the low egg production poultry to raise the egg production rate of newly bred unknown poultry, therefore, it is more accurate and faster than the traditional breeding techniques, thus increases the production value of poultry and reduces the breeding costs.

According to one perspective of the present invention, the present invention may be applied to the breeding industry for experimental organisms, poultry breeding industry or poultry marketing industry, or other related industries. It should be understood by those skilled in the art that, the embodiments mentioned in the present invention are only used to illustrate the present invention, rather than limiting the present invention, and various changes and modifications can be made within the spirit and scope of the present invention.

The present invention provides a poultry selection method to improve the egg production rate, utilizing the advantages of the protein analysis, and the levels of particular serum proteins, select the required poultry according to the egg production rate. In addition, the following advantages are provided by the present invention: (1) raises the egg production ability of poultry: effective selection of the poultry with the required egg production rate can be performed based on the selection methods described in the present invention, and the production value of the selected poultry would be 20% higher than unselected poultry; (2) shortens the breeding period: the methods described in the present invention can be used to perform the selection, based on the estimate of the poultry's egg production ability at the early stage of breeding (14 weeks), thus, reduces approximately 40% of breeding time compared to the traditional method. Moreover, the present invention provides the basis of reference for the poultry breeding industry and researchers in breeding to improve the fecundity of poultry, utilizing the advantages of the protein analysis, and the levels of particular serum proteins, select the required poultry according to the egg production rate, allowing the screening of low egg production poultry to be performed at the early stage of breeding, improve the existing problem of low egg production rate, and increase the economic benefits of the poultry breeding industry and raises the market share, and providing a technology for scientific researches of animals and industry applications.

Although preferred embodiments of the present invention have been described, it will be understood by those skilled in the art that the present invention should not be limited to the described preferred embodiments. Rather, various changes and modifications can be made within the spirit and scope of the present invention, as defined by the following claims.

Having described the invention, the following is claimed:

1. A method of poultry selection to improve the egg production rate, comprising:
   collecting protein sample quantity, concentration level and egg productivity information from multiple groups of poultry;
   transforming said protein sample concentration level of multiple groups of poultry into multiple ratings, and generating codes that correspond to said ratings;
   transforming said protein sample quantity into multiple ranks, and generating codes that correspond to said ranks;
   determining the tendency of said multiple ratings based on the mean and standard deviation of said multiple ratings;
   based on said tendency of multiple ratings and said egg productivity information, determining required selection region, and combine the codes of said ratings and codes of said ranks into regional codes;
   comparing said regional codes to determine code matching rate of multiple groups; and
   selecting poultry with required egg production rate based on said matching rate.

2. The poultry selection method of claim 1, wherein said protein samples include serum proteins.

3. The poultry selection method of claim 2, wherein said serum proteins include Vitellogenin and Apolipoprotein A-I.

4. The poultry selection method of claim 2, wherein said serum proteins include proteins similar to IGF-I.

5. The poultry selection method of claim 2, wherein said serum proteins include Apo VLDL-II.

6. The poultry selection method of claim 2, wherein said serum protein samples include proteins related to egg production rates.

7. The poultry selection method of claim 1, wherein said poultry comprises different types of egg-laying poultry including chickens, ducks, geese and birds.

8. The poultry selection method of claim 1, wherein said multiple groups of poultry include different groups of said poultry, from birth to 48 weeks of age.

9. The poultry selection method of claim 1, wherein said multiple groups of poultry include different groups of said poultry with the ages of 14, 24 and 35 weeks.

10. The poultry selection method of claim 1, wherein said egg productivity information include the rate of egg production ability.

11. The poultry selection method of claim 1, wherein said step of transforming protein sample quantity into multiple ranks further include: when quantity of protein samples of said multiple groups of poultry are different, the ratio of said sample quantity between said multiple groups of poultry can be used to transform into said multiple ranks.

12. The poultry selection method of claim 1, wherein said step of determining said selection region further include: when said multiple ratings between said multiple groups of poultry are different, ratings adjacent to said multiple ratings can be used as the basis to help with the determination of said selection region.

13. A method of poultry selection to improve the egg production rate, comprising:
   collecting and ranking of protein samples and related egg productivity information of known and unknown poultry groups to sort out ratings;
   within the information of said known poultry groups, select a poultry group with a required egg production rate;
   defining regional codes based on said ratings of known poultry groups;
   comparing ratings of said known poultry groups and said unknown poultry groups, and selecting poultry with the same regional codes as said poultry group with said required egg production rate from said unknown poultry groups; and
   based on the comparison results of said regional codes' matching rates, selecting said poultry with said required egg production rate.

14. The poultry selection method of claim 13, wherein said steps of collecting protein samples and egg productivity information of unknown and unknown groups include collecting protein samples' quantity, concentration level and egg productivity information.

15. The poultry selection method of claim 13, wherein said protein samples include serum proteins.

16. The poultry selection method of claim 15, wherein said serum protein include Vitellogenin and Apolipoprotein A-I.

17. The poultry selection method of claim 15, wherein said serum proteins include proteins similar to IGF-I.

18. The poultry selection method of claim 15, wherein said serum proteins include Apo VLDL-II.

19. The poultry selection method of claim 15, wherein said serum protein samples include proteins related to egg production rates.

20. The poultry selection method of claim 13, wherein said poultry comprises different types of egg-laying poultry including chickens, ducks, geese and birds.

21. The poultry selection method of claim 13, wherein said multiple groups of poultry include different groups of said poultry, from birth to 48 weeks of age.

22. The poultry selection method of claim 13, wherein said multiple groups of poultry include different groups of said poultry with the ages of 14, 24 and 35 weeks.

23. The poultry selection method of claim 13, wherein said egg productivity information include the rate of egg production ability.

24. The poultry selection method of claim 13, wherein said steps of ranking to sort out the ratings is ranked according to the size of said information.

25. The poultry selection method of claim 13, wherein said ratings are vector values.

26. The poultry selection method of claim 13, wherein said steps of comparing the vector values of said known poultry groups and said unknown poultry groups include: when different regional codes comprise the same poultry, the regional code that appeared first is selected.

27. The poultry selection method of claim 13, wherein said steps of comparing the matching rates of said regional codes include when said known poultry group and said unknown poultry group have the same regional codes, said unknown poultry is determined as the poultry with the required egg production rate.

* * * * *